United States Patent
Iimura et al.

(10) Patent No.: US 6,642,439 B2
(45) Date of Patent: Nov. 4, 2003

(54) BASIDIOMYCETE MANGANESE PEROXIDASE GENE-TRANSFERRED PLANT AND A METHOD FOR REMOVING AN ENVIRONMENTAL CONTAMINANT USING THE SAME

(75) Inventors: Yosuke Iimura, 108-1/4-104, Hitachinohigashi, 394-1, Shimone-machi, Ushiku-shi, Ibaraki 300-1203 (JP); Yoshihiro Katayama, Tokyo (JP)

(73) Assignees: Agency of Industrial Science and Technology, Tokyo (JP); Yosuke Iimura, Ibaraki (JP)

( * ) Notice: Subject to any disclaimer, the term of this patent is extended or adjusted under 35 U.S.C. 154(b) by 125 days.

(21) Appl. No.: 09/748,264

(22) Filed: Dec. 27, 2000

(65) Prior Publication Data

US 2002/0083492 A1 Jun. 27, 2002

(30) Foreign Application Priority Data

Jul. 25, 2000 (JP) ........................................ 2000/223653

(51) Int. Cl.$^7$ .................... C12N 15/09; C12N 15/31; C12N 15/82; A01H 5/00
(52) U.S. Cl. ..................... 800/288; 800/278; 800/298; 435/69.1; 435/419; 435/468; 536/23.6; 536/24.1
(58) Field of Search ................................. 800/278, 288, 800/298; 435/468, 419, 69.1; 536/23.6

(56) References Cited

PUBLICATIONS

Lazar et al, "Transforming Growth Factor X: Mutation of Aspartic Acid 47 and Leucine 48 Results in Different Biological Activities", Mar. 1988, Molecular and Cellular Biology vol. 8 No. 3, pp. 1247–1252.*
Broun et al, "Catalytic Plasticity of Fatty Acid Modification Enzymes Underlying Chemical Diversity of Plant Lipids", Nov. 1998, Science vol. 282, pp 1315–1317.*
Asada et al., "Structures of Genomic and Complementary DNAs Coding for Pleurotus Ostreatus Manganese (II) Peroxidase," *Biochimica et Biophysica Acta*, 1251, pp. 205–209 (1995).
Black et al., "Cloning and Characterization of a Lignin Peroxidase Gene From The White–Rot Fungus Trametes Versicolor", *Biochemical and Biophysical Research Communications*, vol. 179, pp. 428–435 (1991).
Bogan et al., Polycyclic Aromatic Hydrocarbon–Degrading Capabilities of Phanerochaete Laevis HHB–1625 and Its Extracellular Ligninolytic Enzymes, *Applied and Environmental Microbiology*, vol. 62, pp. 1597–1603 (1996).
Bumpus et al., "Biodegradation of Environmental Pollutants by the White Rot Fungus Phanerochaete Chrysosporium: Involvement of the Lignin Degrading System," *BioEssays*, vol. 6, pp. 166–170.

Cunningham et al., "Phytoremediation of Contaminated Soils," *Tibtech*, vol. 13, pp. 393–397 (1995).
de Souza et al., "Rhizosphere Bacteria Enhance Selenium Accumulation and Volatilization by Indian Mustard," *Plant Physiology*, vol. 119, pp. 565–573 (1999).
Dobson et al., "Hopes for the Future: Restoration Ecology and Conservation Biology," *Science*, vol. 277, pp. 515–522 (1997).
Johansson et al., The Gene From the White–Rot Fungus Trametes Versicolor Encoding the Lignin Peroxidate Isozyme LP7, *Biochimica et Biophysica Acta*, 1263, pp. 71–74 (1995).
Morikawa et al., "More Than a 600–Fold Variation in Nitrogen Dioxide Assimilation Among 217 Plant Taxa," *Plant, Cell and Environment*, vol. 21, pp. 180–190 (1998).
Murashige et al., "A Revised Medium for Rapid Growth and Bio Assays with Tobacco Tissue Cultures," *Physiol. Plant*, vol. 15, pp. 473–496 (1962).
Newman et al., "Phytoremediation of MTBE at a California Naval Site," *Soil & Groundwater Cleanup*, pp. 42–45. Feb./Mar. (1999).
Novotny et al., "Extracellular Oxidative Enzyme Production and PAH Removal in Soil by Exploratory Mycelium of White Rot Fungi," *Biodegradation*, vol. 10, pp. 159–168 (1999).
Pradhan et al., "Isolation, Characterization and Baculovirus–Mediated Expression of the cDNA Encoding Cytosine DNA Methyltransferase From Pisum Sativum," *Nucleic Acids Research*, vol. 26, pp. 1214–1222 (1998).
Pribnow et al., "Characterization of a cDNA Encoding a Manganese Peroxidase, from the Lignin–Degrading Basidiomycete Phanerochaete Chrysosporium," *The Journal of Biologicval Chemistry*, vol. 264, pp. 5036–5040 (1989).
Reddy et al., A Two–Component Tetrachlorohydroquinone Reductive Dehalogenase System from the Lignin–Degrading Basidiomycete Phanerochaete Chrysosporium, *Biochemical and Biophysical Research Communications*, vol. 257, pp. 901–905 (1999).
Reddy et al., "Degradation of 2,4,6–Trichlorophenol by Phanerochaete Chrysosporium: Involvement of Reductive Dechlorination," *Journal of Bacteriology*, vol. 180, pp. 5159–5164 (1998).
Saloheimo et al., "A Lignin Peroxidase–Encoding cDNA from the White–Rot Fungus Phlebia Radiata: Characterization and Expression in Trichoderma Reesei," *Gene*, vol. 85, pp. 343–351 (1989).

(List continued on next page.)

Primary Examiner—Elizabeth F. McElwain
Assistant Examiner—Medina A. Ibrahim
(74) Attorney, Agent, or Firm—Finnegan, Henderson, Farabow, Garrett & Dunner, L.L.P.

(57) ABSTRACT

The present invention relates to a plant into which DNA encoding a basidiomycete-derived peroxidase is transferred, said DNA being expressed therein, and to a method for decomposing and removing hazardous chemicals in an environment effectively by using the plant.

18 Claims, 10 Drawing Sheets

PUBLICATIONS

Shiota et al., "Herbicide–Resistant Tobacco Plants Expressing the Fused Enzyme Between Rat Cytochrome P4501A1 (CYP1A1) and Yeast NADPH–Cytochrome P450 Oxidoreductase," *Plant Physiol.,* vol. 106, pp. 17–23 (1994).

Tien et al., "Cloning and Sequencing of a cDNA for a Ligninase From Phanerochaete Chrysosporium," *Nature,* vol. 326, pp. 520–523 (1987).

Valli et al., "Degradation of 2, 7–Dichlorodibenzo–p–Dioxin by the Lignin–Degrading Basidiomycete Phanerochaete Chrysosporium," *Journal of Bacteriology,* vol. 174, pp. 2131–2137 (1992).

Nagata et al., "Production of Transgenic Plant Having *Sphingomonas Paucimobilis* UT26–Derived γ–HCH Dehydrochlorinase Gen (linA)," *Nippon Nogeikagaku Kaisha,* vol. 71 (Eap6), p. 89 (1997).

English Translation of Nagata et al., *Nippon Nogeikagaku Kaishi,* vol. 71 (Eap6), p. 89 (1997).

Asano et al., "Expression in Tobacco Plant of hadA and hadB Genes Involved in 2,4,6–Trichlorophenol Degradation by *Burkholderia Pickettii,*" *Nippon Nogeikagaku Kaishi,* vol. 72 (2D1p22), p. 164 (1998).

English Translation of Asano et al., *Nippon Nogeikagaku Kaishi,* vol. 72 (2D1p22), p. 164 (1998).

Asada, Y. et al., "Structures of Genomic and Complementary DNA's Coding for *Pleurotus ostreatus* Manganese (II) Peroxidase," *Biochimica et Biophysica Acta,* vol. 1251 pp. 205–209 (1995).

Camarero, S. et al., "The Cloning of a New Peroxidase Found in Lignocellulose Cultures of *Pleurotus eryngii* and Sequence Comparison with Other Fungal Peroxidases," *FEMS Microbiology Letters,* vol. 191, pp. 37–43 (2000).

Godfrey, B. et al., "Characterization of a Gene Encoding a Manganese Peroxidase From *Phanerochaete chrysosporium,*" *Gene,* vol. 93, pp. 119–124 (1990).

Gold, M. et al., "Manganese Peroxidase," *Metal Ions in Biological Systems,* vol. 37, Edited by Astrid Siegel (1973).

Johansson et al., "A Cluster of Genes Encoding Major Isozymes of Lignin Peroxidase and Manganese Peroxidase from the White–rot Fungus *Trametes versicolor,*" *Gene,* vol. 170. pp. 31–38 (1996).

Mayfield, M et al., "Characterization of the mnp2 Gene Encoding Manganese Peroxidase Isozyme 2 from the Basidiomycete *Phanerochaete chrysosporium,*" *Gene,* vol. 142, pp. 231–235 (1994).

Miyauchi, K. et al., "Cloning and Sequencing of 2,5–Dichlorohydroquinone Reductive Dehalogenase Gene Whose Product Is Involved in Degradation of γ–Hexachlorocyclohexane by *Shingomonas paucimobilis,*" *Journal of Bacteriology,* vol. 180, pp. 1354–1359 (1998).

Nagata, Y. et al., "Two Different Types of Dehalogenases, LinA and LinB, Involved in γ–Hexachlorocyclohexane Degradation in *Sphingomonas paucimobilis* UT26 are Localized in the Periplasmic Space Without Molecular Processing," *Journal of Bacteriology,* vol. 181, pp. 5409–5413 (1999).

Ruiz–Duenas, F.J. et al., "A New Versatile Peroxidase from *pleurotus,*" *Biochemical Society Transactions,* vol. 29, pp. 116–122 (2001).

Tello, M. et al., Characterization of Three New Manganese Peroxidase Genes from the Ligninolytic Basidiomycete *Ceriporiopsis subvermispora, Biochimica et Biophysica Acta,* vol. 1490, pp. 137–144 (2000).

* cited by examiner

FIG.1

```
   1 ATGGCTTTCAAAACTCTCGCCTCTCTCCTCTCGGTTCTGGTCACCATCCAGGTCGCAAGC    60
   1  M  A  F  K  T  L  A  S  L  L  S  V  L  V  T  I  Q  V  A  S    20

61 GGCGCGCTCACCCGCCGTGTCGCCTGCCCCGACGGCGTGAACACCGCTACCAACGCGGCG   120
  21  G  A  L  T  R  R  V  A  C  P  D  G  V  N  T  A  T  N  A  A    40

121 TGCTGCCAGCTCTTCGCTGTCCGCGACGACATCCAGCAGAACCTGTTCGATGGCGGCGAG   180
  41  C  C  Q  L  F  A  V  R  D  D  I  Q  Q  N  L  F  D  G  G  E    60

181 TGTGGCGAGGAGGTCCACGAGTCCCTCCGTCTGACCTTCCACGACGCCATCGGCATCTCT   240
  61  C  G  E  E  V  H  E  S  L  R  L  T  F  H  D  A  I  G  I  S    80

241 CCTTCCATCGCCTCCCGCGGCCAATTCGGGGGCGGAGGTGCCGACGGCTCCATCGCCCTC   300
  81  P  S  I  A  S  R  G  Q  F  G  G  G  G  A  D  G  S  I  A  L   100

301 TTTGAGGACATCGAGACCAACTTCCACGCCAACCTCGGTGTCGACGAGATCATCGACGAG   360
 101  F  E  D  I  E  T  N  F  H  A  N  L  G  V  D  E  I  I  D  E   120

361 CAGCGGCCGTTCATCGCCCGCCACAACCTCACCACCGCCGACTTCATCCAGTTCGCCGGC   420
 121  Q  R  P  F  I  A  R  H  N  L  T  T  A  D  F  I  Q  F  A  G   140

421 GCCATCGGTGTCAGCAACTGCCCCGGCGCGCCCCAGCTGGACGTGTTCATCGGCCGCCCC   480
 141  A  I  G  V  S  N  C  P  G  A  P  Q  L  D  V  F  I  G  R  P   160

481 GACGCGACGCAGCCCGCGCCCGACCTGACCGTGCCCGAGCCGTTCGACACCGTCGACAGC   540
 161  D  A  T  Q  P  A  P  D  L  T  V  P  E  P  F  D  T  V  D  S   180

541 ATCATCGAGCGGTTCTCCGACGCGGGCGGCTTCACGCCCGCGGAGATCGTCGCGCTTCTC   600
 181  I  I  E  R  F  S  D  A  G  G  F  T  P  A  E  I  V  A  L  L   200

601 GTGTCGCACACGATCGCCGCGGCCGACCACGTCGACCCGAGCATCCCCGGAACGCCCTTC   660
 201  V  S  H  T  I  A  A  A  D  H  V  D  P  S  I  P  G  T  P  F   220

661 GACTCGACCCCGGAGGAGTTCGACACGCAGTTCTTCATCGAGACGCAGCTCCGCGGCACG   720
 221  D  S  T  P  E  E  F  D  T  Q  F  F  I  E  T  Q  L  R  G  T   240

721 CTCTTCCCCGGCACCGGCGGCAACCAGGGCGAGGTCGAGTCCCCCCTCCGCGGCGAGCTG   780
 241  L  F  P  G  T  G  G  N  Q  G  E  V  E  S  P  L  R  G  E  L   260

781 CGCCTCCAGTCCGACTCTGAGCTCGCGCGCGACTCTCGCACTGCTTGCGAGTGGCAGTCC   840
 261  R  L  Q  S  D  S  E  L  A  R  D  S  R  T  A  C  E  W  Q  S   280

841 TTCGTCAACAACCAGGCCAAGCTCCAGTCCGCGTTCAAGGCTGCCTTCCGCAAGATGACC   900
 281  F  V  N  N  Q  A  K  L  Q  S  A  F  K  A  A  F  R  K  M  T   300

901 GTGCTCGGCCACGACGAGAGCCTGCTGATCGAGTGCTCCGAGCTCGTGCCCACGCCTCCG   960
 301  V  L  G  H  D  E  S  L  L  I  E  C  S  E  L  V  P  T  P  P   320

961 CCGGCGACGAGCGTCGCGCACTTCCCCGCTGGGCTCAGCAACGCCGACGTCGAGCAGGCG  1020
 321  P  A  T  S  V  A  H  F  P  A  G  L  S  N  A  D  V  E  Q  A   340

1021 TGCGCCGACACCCCCTTCCCGACGCTCCCCACCGACCCTGGACCCGTCACCACCGTCGCC  1080
 341  C  A  D  T  P  F  P  T  L  P  T  D  P  G  P  V  T  T  V  A   360

1081 CCCGTCCCCCCGTCGTAA                                             1098
 361  P  V  P  P  S  *                                              366
```

```
  1: MAPKTLASLLSVL-VTIQVASGA-LTRRVA-CPDGVNTATNAACCQLPAVRDDIQQNLFD   57
 58: GGECGEEVHESLRLTPHDAIGISPSIASRGQFGGGADGSIALFEDIETNPHANLGVDEI  117
118: IDEQRPFIARH-NLTTADFIQFAGAIGVSNCPGAPQLDVFIGRPDATQPAPDLTVPSPFD  176
177: TVDSITERFSEPGGPTPAEIVALLVSHTIAAADHVDPSIPGTPPDSTPEEPDTQPPIRTQ  236
237: LRGTLPPGTGGMQGEVESPL--------RGELRLQSDSELARDSRTACEWQSFVNNQAKLQ  289
290: SAPKAAPRKMTVLGHDESLLIECSELVPTP-PPATSVGNFPAGLSNADVEQ-ACADTPPP  347
348: TLPTDPGPVTT-----------VAPVPPS                                  365
```

■ : distal alginine
● : proximal histidine

*1) A hyphen shows a gap to other homologous manganese peroxidase.
*2) A boldfaced amino acid is conserved compared with that of other manganese peroxidase.

FIG. 2

BASIDIOMYCETE MANGANESE PEROXIDASE GENE-TRANSFERRED PLANT AND A METHOD FOR REMOVING AN ENVIRONMENTAL CONTAMINANT USING THE SAME

FIELD OF THE INVENTION

The present invention relates to a plant into which DNA encoding a basidiomycete-derived peroxidase is transferred, and to a method for decomposing and removing hazardous chemicals using said plant.

BACKGROUND OF THE INVENTION

Physical and chemical treatments have been developed as technologies to treat the industrially produced chemical substances, PCB, BHC and DDT, or the unintentional product, dioxin, when they are present or accumulated at high concentration in an environment. For example, techniques such as photochemical decomposition, supercritical water decomposition, solvent extraction decomposition, catalytic oxidation, vapor phase hydrogenation reduction, melt combustion, heat treatment in reducing atmosphere, and glassification treatment, have been experimentally tested. However, those physical and chemical treatments seem to be impractical in view of cost-efficiency for hazardous chemicals accumulated at low levels in the environments as in soils or rivers, and moreover, in-situ treatments are required. Even when the concentration of these extensively diffused substances is low, the level is enough for endocrine disturbance. As a means to overcome this problem, bio-remediation has been performed with the use of microorganisms that strongly decompose hazardous chemicals. Such decontamination by microorganisms also has problems. That is, to maintain such microorganisms predominantly over the long term, the inoculation of microorganisms and application of nutrients are essential, which becomes more difficult as the area of contamination expands.

Under these circumstances, an attempt has been made recently for decontamination by phyto-remediation (restoration of the environment by plants) using plants.

Plants can be grown independently taking nourishment from the sun, water, and inorganic ions, and can be cultivated extensively by controlling seeds. Because of this, plants have attracted attention as a method for long-lasting environmental decontamination.

Studies on phyto-remediation to agricultural chemicals (Plant physiol, 106, 17, 1994), heavy metals (Trends Biotech, 13, 393, 1995), organic mercury (Nature Biotechnol, 16, 925–928, 1998), selenium (Plant Physiol, 119, 565–573, 1999), MTBE of a gasoline additive (Soil & Groundwater Cleanup February/March, 42–45, 1999), nitrogen oxides (Plant, Cell & Environment, 21, 180–190, 1998), and radioactive compounds (Science, 277, 515–522, 1997), have been made so far. Further study concerns the remediation of contaminated soils by cooperation of plants and rooting zone microorganisms comprising enhancing growth of soil microorganisms or an improvement of flora by cultivating plants in contaminated soils.

The phyto-remediation that has been examined, includes use of the detoxification mechanism or evaporation ability which plants originally bear. Moreover, an attempt has been made to enhance the environmental decontamination function of plants by transferring genes from microorganisms.

The environmental remediation by gene recombinant plants, in the case of for example organic mercury, is carried out by reducing the organic mercury to a metal mercury and vaporizing it in the atmosphere. In the case of agricultural chemicals or heavy metals, the remediation is carried out by transport to and accumulation in cell wall fraction. However, because the accumulated environmental contaminants are released again in the environment through blighting of plants, said remediation does not contribute to fundamental decontamination. Furthermore, in the case of dioxin or PCB, it is predictable that readily degradable substances are decomposed while non-degradable and highly toxic substances are condensed and accumulated. Therefore, it is thought that conventional phyto-remediation is insufficient.

As detailed above, an attempt to decompose hazardous chemicals directly in plant cells using recombinant plants into which an enzyme gene for decomposing hazardous chemicals derived from microorganisms is transferred, has been made with respect to the decomposition of 2,4,6-trichlorophenol (Japan Society for Bioscience, Biotechnology, and Agrochemistry, Abstracts for the Annual Meeting, p146, 1998) or γ-hexachlorocyclohexane (Japan Society for Bioscience, Biotechnology, and Agrochemistry, Abstracts for the Annual Meeting, p89, 1997).

Incidentally, the basidiomycete-derived peroxidase gene has two types of families, lignin peroxidase gene (LiP) and manganese peroxidase gene (MnP). These genes were isolated from various basidiomycetes, such as *Phanerochaete chrysosporium, Phlebia radiata*, Coriolus and Pleurotus, and the primary structures thereof were determined (Nature, 1987. 326, 520–523, Nucelic Acid Res, 1988, 16, 1219, Gene, 1989, 85, 343–351, Biochem Biopys Res Commun, 1991, 179, 428–435, J Biol Chem, 1989, 264, 5036–5040, Biochim Biophys Acta, 1995, 1263, 71–74, Biochim Biophys Acta, 1251, 205–209). It has been demonstrated that enzymes encoded by these genes decompose a variety of chemical substances which are not readily degradable. The enzymes oxidatively decompose endocrine-disturbance substances including polycyclic aromatic hydrocarbons (Biodegradation, 1999, 10, 159–168, Appl Environ Microbiol, 1996, 1597–1603), chlorophenols (Biochem Biophys Res Commun, 1999, 257, 901–905, J Bacteriol, 1998, 180, 5159–5164) and dioxin (BioEssays, 1986, 6, 166–170, J Bacteriol, 1992, 174, 2131–2137), etc.

As described above, the basidiomycete-derived peroxidase oxidatively decomposes various hazardous chemicals; therefore, if a plant capable of exerting the effect of this enzyme could be prepared, it would be very useful for decomposing and removing hazardous chemicals in the environment.

However, the preparation of such plants is predicted to be difficult for the following reasons.

1) The production of a basidiomycete-derived peroxidase as a stable and active protein in plant cells is known to be difficult because of high GC content of the peroxidase gene and the codon usage, and there are no successful examples.

2) Even if the difficulty described in 1) is overcome, it was predicted to be difficult to produce a plant capable of decomposing and removing hazardous chemicals in the environment effectively, because in general, environmental contaminants are highly fat-soluble (or lipophilic) chemical compounds, and because for example PCB or dioxin is absorbed from the roots of plants and the amount taken-up within plant cells is very small. Furthermore, it was estimated that obtaining transformed plants capable of effectively decomposing and removing chemical compounds as described above was difficult unless the function of the peroxidase is expressed on the cell surface of plant roots.

3) Generally, hydrogen peroxide is considered to exist on the surface layer of plant cells. However, even when transformed plants with functions described in 2) can be obtained, the reaction system for decomposition of hazardous chemicals is difficult to make it to function unless the production and distribution of hydrogen peroxide in the plant and the basidiomycete-derived peroxidase produced by gene transfer, are synchronized spatially and temporally.

Under the technical backgrounds described above, an object of the present invention is to provide a plant capable of decomposing and removing hazardous chemicals in the environment effectively.

SUMMARY OF THE INVENTION

The inventors have gained the following findings after extensible and intensive studies for solving above problems.

1) Since the basidiomycete-derived peroxidase produced by gene transfer exists in an active and stable form on the cell surface of transgenic plant roots, hazardous chemicals are decomposed by the peroxidase in the rooting zone even when the peroxidase is not incorporated within cells.

2) Since endogenous hydrogen peroxide exists in plant bodies and is released from roots synchronously with production of the peroxidase, hazardous chemicals can be decomposed without adding hydrogen peroxide externally.

The present invention has been completed based on the above findings.

More specifically, the present invention relates to a plant into which DNA encoding the basidiomycete-derived peroxidase is transferred, said DNA being expressed therein.

Furthermore, the present invention relates to a method for decomposing and removing hazardous chemicals, comprising cultivating the above plant in the environment contaminated with hazardous chemicals.

BRIEF DESCRIPTION OF THE DRAWINGS

FIG. 1 shows the nucleotide sequence of a manganese peroxidase gene derived from Coriolus, and the deduced amino acid sequence.

FIG. 2 shows the amino acid sequence deduced from the nucleotide sequence of the manganese peroxidase gene from Coriolus.

DETAILED DESCRIPTION OF THE INVENTION

Figure 3:
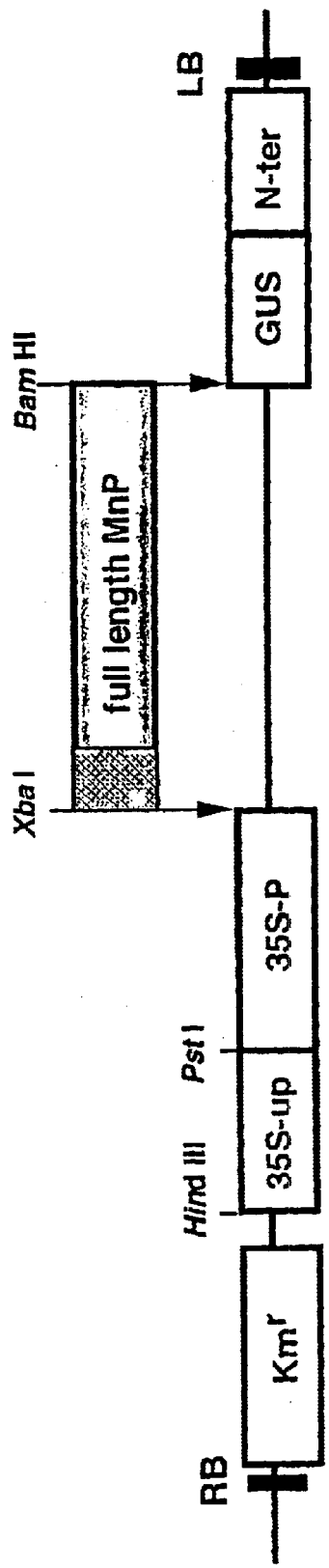
FIG. 3 shows the structure of a plasmid W35SfMnP/pBI121.

The present invention will be described in detail as follows.

The plant of the present invention is a plant into which DNA encoding a basidiomycete-derived peroxidase is transferred, said DNA being expressed therein.

The basidiomycete-derived peroxidase includes not only a natural protein having peroxidase activity obtained from basidiomycete, but also a protein which comprises one or more amino acid by substitutions, deletions, and additions relative to the natural protein and has peroxidase activity. Examples of the basidiomycete-derived peroxidase include lignin peroxidase and manganese peroxidase. Used as the manganese peroxidase are a protein represented by the amino acid sequence of SEQ ID No:2, and a protein which comprises one or more amino acid by substitutions, deletions and additions and has peroxidase activity.

Gene cloning methods can be used to isolate the DNA encoding a basidiomycete-derived peroxidase. For example, there is a method where an enzyme is purified, an amino acid sequence is determined, and synthetic nucleotides are prepared based on said sequence to select said DNA from a gene library by hybridization. Moreover, there is also a method in which primers used for PCR (Polymerase Chain Reaction) are prepared based on the known gene base sequence information without purifying the enzyme to amplify and isolate a specific region or whole region of the gene by performing PCR.

The DNA encoding a basidiomycete-derived peroxidase, can be expressed by transferring it into plants with a suitable promoter or the like. As an example of the promoter, cauliflower mosaic virus 35S promoter (CMV35SP) can be given, but further enhancement of expression can be expected by inserting a non-translational region (CMV35SP) upstream of the CMV35SP, to the upstream of this promoter. Furthermore the use of a promoter which specifically functions in plant roots, is considered to be all the more effective. Any terminator could be used so long as it functions in plant cells, for example, the terminator of a nopaline synthase enzyme gene can be given as an example. For DNA transfer into plants, chemical, physical and biological methods including electroporation, a method using a particle gun, and a method using Agrobacterium can be used to transfer DNA into a plant genome. Plant cells into which DNA is transferred, can be selected and redifferentiated by the use of a drug-resistant property of antibiotics and the like.

The plants available in the present invention can be applied to any type of plants so long as the redifferentiating method from cells, tissues or organs is established and the gene transfer system is constructed. Examples of preferable plant species include seed plants. The seed plants can be either herby plants or woody plants.

Since there exist the basidiomycete-derived peroxidase and hydrogen peroxide in extracellular layers of the plant prepared as above, hazardous substances can be decomposed and removed in the rooting zone continuously and independently by cultivating this plant in the environment contaminated with hazardous chemicals. As used herein, the term "hazardous chemicals" means substances indicating toxicity or endocrine disturbance to human bodies, and substances able to be decomposed by the basidiomycete-derived peroxidase. To be more specific, examples include chlorophenol, dioxin, agricultural chemicals, polycyclic aromatic hydrocarbons, an alkylphenol, aromatic hydrocarbons, and nitro compounds. Additionally, the term "environment" means, for example, soils, wetlands, rivers and the like.

As described above, since endogenous hydrogen peroxide exists in plants as described above, addition of hydrogen peroxide from outside is not required. When manganese peroxidase is used as the basidiomycete-derived peroxidase, however, the addition of Mn (II) is necessary for decomposing hazardous chemicals.

EXAMPLES

Example 1

Cloning of cDNA Encoding the Manganese Peroxidase from Coriolus

To isolate cDNA encoding the manganese peroxidase form Coriolus (*Coriolus versicolor* IF030340), highly conserved amino acid sequences were determined by comparing to amino acid sequences for the manganese peroxidase genes from basidiomycetes (*Phanerochaete chrysosporium* ME446, *Trametes versicolor* PRL572 and *Pleurotus ostreatus*), which had been already reported. Among them, amino acid sequences at the upstream and downstream regions was selected, and the oligonucleotides corresponding to these amino acid sequences were chemically synthesized.

PCR was performed using the oligonucleotides prepared as above as primers, and cDNA of Coriolus as a template. 25 cycles of 30 sec at 94° C., 30 sec at 55° C., 90 sec at 72° C. were performed for the reaction. Pyrobest DNA polymerase (Takara Shuzo Co., Ltd.) was used for the reaction. The DNA amplification product with an expected size was confirmed by subjecting an aliquot of the reaction mixture to 1.5% agarose gel electrophoresis. The amplified fragment was excised and extracted from the agarose to be used for its sequencing. Based on the nucleotide sequence of the amplified fragment determined by a dideoxy chain termination method, a full-length cDNA comprising the previously amplified fragment was obtained by 5' RACE and 3' RACE (FIG. 1).

As a result of homology analysis of the amino acid sequence (CvMnP) deduced from the nucleotide sequence of said cDNA, it had 48.8%, 47.7% homology to the manganese peroxidases of *Phanerochaete chrysosporium* ME446, PcMnP1 and PcMnP2 respectively. It showed 54.6% homology to the manganese peroxidase of *Pleurotus ostreatus* (PoMnP). Furthermore, 99.5% holomogy was observed to the manganese peroxidase of *Trametes versicolor* PRL572 (TvMnP). Still further, distal and proximal histidines and a distal arginine considered to be essential for peroxidase activity, were conserved (FIG. 2), thus it was concluded that said cDNA encodes the manganese peroxidase from Coriolus.

Example 2

Construction of a Vector and Transfer of the Same into a Plant

The primers were synthesized in order to obtain manganese peroxidase cDNA into which restriction enzyme sites were introduced, and cDNA encoding a mature manganese peroxidase. The nucleotide sequences of the synthesized primers are as follows. The mature manganese peroxidase comprises deletion of 26 N-terminal amino acid residues when compared to the full-length manganese peroxidase shown in FIG. 1.

MpfXb:5'-ttgtttctagatggctttcaaaactctcgc-3'(SEQ ID NO:3).

MpmXb:5'-aatctctagatggtcgcctgcccctacggagtg-3'(SEQ ID NO:4).

MpBa:5'-aaftggatccttacgacgggggggacgggggg-3'(SEQ ID NO:5).

The PCR was performed using Pyrobest DNA polymerase, the synthesized DNAs as primers, and the manganese peroxidase cDNA shown in FIG. 1 as a template. 30 cycles of 10 sec at 98° C., 30 sec at 60° C. and 80 sec at 72° C. were performed for the reaction. The fragment in which Xba I and Bam HI were added to the full-length manganese peroxidase cDNA, was obtained, and this was inserted into pCR 2.1. In the same manner, a cDNA fragment encoding the mature manganese peroxidase, was obtained using MpmXb (SEQ ID NO:4) and MpBa (SEQ ID NO:5), and inserted into pCR 2.1. Furthermore, the same operation as in the above was carried out using MpfXb (SEQ ID NO:3) and MnHisR (SEQ ID NO:6), or MpmXb (SEQ ID NO:4) and MnHisR (SEQ ID NO:6), as primers, so that a histidine tag was added to the C-terminus after transcription and translation of the introduced gene. The nucleotide sequence of MnHisR (SEQ ID NO:6) is as follows: 5'-aattggatcc tcagtggtgg tggtggtggt ggtgcgacgg ggggacgggg gcgacggtgg tgacg-3'(SEQ ID NO:6).

Each nucleotide sequence was confirmed by sequencing.

cDNA fragment amplified above was excised from pCR 2.1, and was inserted into the Xba I, Bam HI sites of pBI221. Each plasmid was named fMnP/pBI221, mMnP/pBI221, fMnP6×His/pBI221 and mMnP6×His/pBI221 respectively.

An attempt was made to enhance the expression efficiency of the manganese peroxidase gene by inserting CMV35SUP into the Hind III, Pst I sites of these plasmids. These plasmids were named W35SfMnP/pBI221, W35SmMnP/pBI221, W35SfMnP6×His/pBI221 and W35SmMnP6×His/pBI221 respectively.

Figure 4:
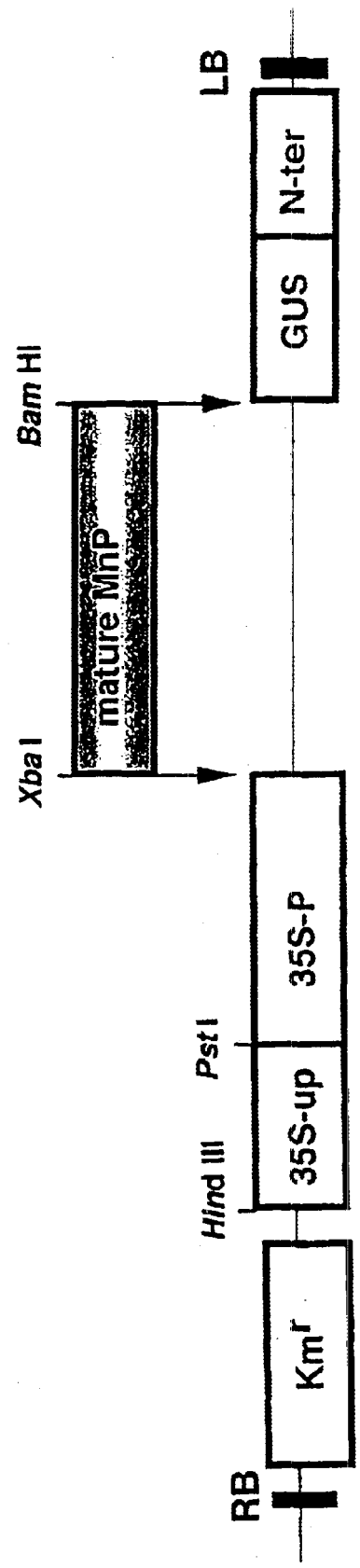
FIG. 4 shows the structure of a plasmid W35SmMnP/pBI121.
Figure 5:
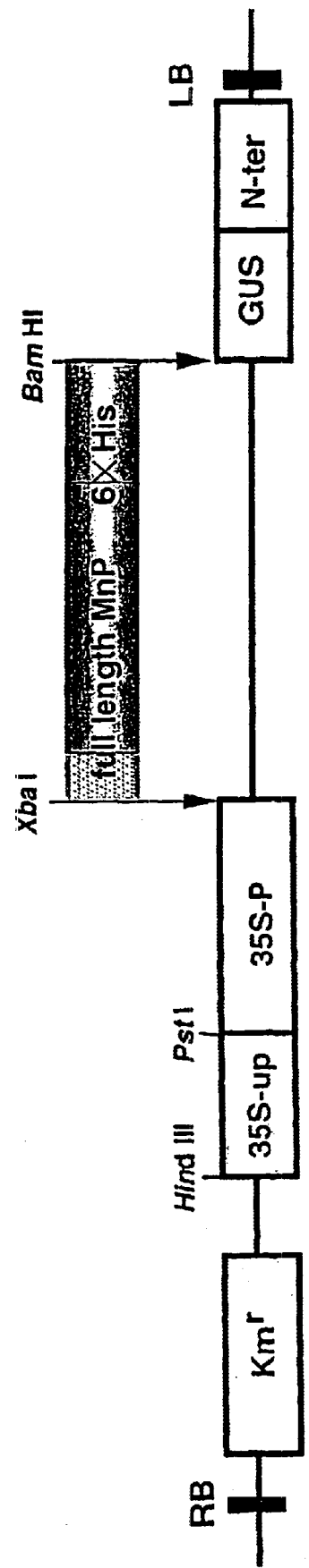
FIG. 5 shows the structure of a plasmid W35SfMnP6×His/pBI121.
Figure 6:
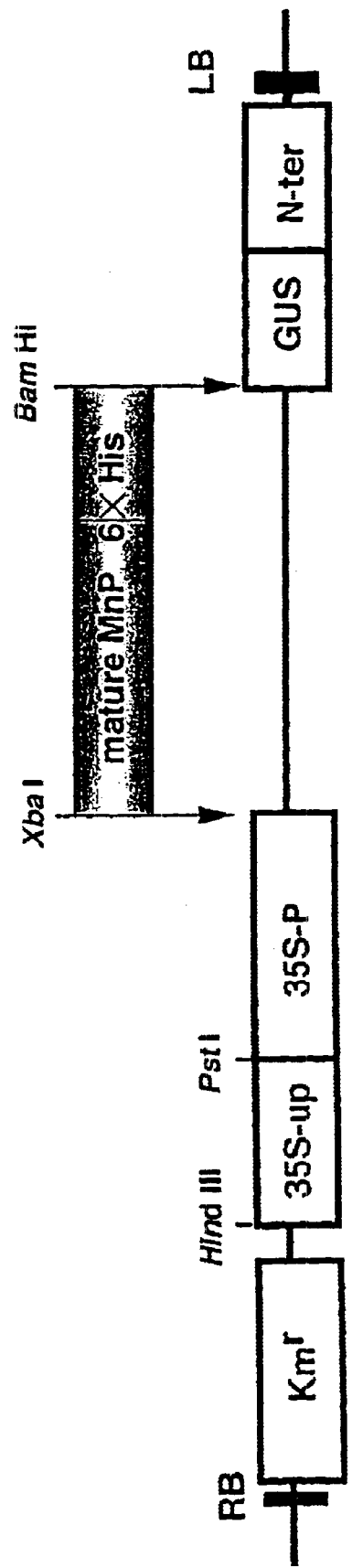
FIG. 6 shows the structure of a plasmid W35SmMnP6×His/pBI121.

Plasmids, W35SfMnP/pBI221, W35SmMnP/pBI221, W35SfMnP6×His/pBI221 and W35SmMnP6×His/pBI221pBI221 were digested with Hind III and Bam HI, and the fragments comprising those manganese peroxidase genes were inserted into Hind III, Bam HI sites of pBI121. Those plasmids were named W35SfMnP/pBI121(FIG. 3), W35SmMnP/pBI121(FIG. 4), W35SfMnP6×His/pBI121 (FIG. 5) and W35SmMnP6×His/pBI221pBI121(FIG. 6) respectively.

A transformed plant was obtained by transferring each manganese peroxidase gene into *Nicotiana tabacum* SR1 strain using an *Agrobacteriun tumefaciens* LBA4404 strain which carries W35SfMnP/pBI121, W35SmMnP/pBI121, W35SfMnP6×His/pBI121, W35SmMnP6×His/pBI121, or pBI121 (as a control). Furthermore, a transformed plant was obtained using the *Agrobacterium tumefaciens* LBA4404 strain carrying pBI121, which was used as a control. Southern analysis and PCR analysis were performed with the total DNA from each individual to confirm that each gene had been transferred.

Example 3

Detection of Manganese Peroxidase Activity in a Callus Induced from a Transformed Plant.

Each transformed callus was induced, and callus of the same wet mass in a Murashige & Skoog complete medium (Plant Physiol, 1962, 15, 473) was incubated at 28° C. for 3 days. The callus of the same wet mass was washed 3 times in 50 mM malonate buffer (pH 4.5), and suspended in a fresh malonate buffer. Manganese sulfate was added to this suspension to a final concentration of 1 mM, which was then incubated at 37° C. for 16 hours. A certain quantity of the culture supernatant was diluted with the malonate buffer to measure an ultraviolet absorption spectrum.

The manganese peroxidase generates a trivalent manganese (Mn(III)) in the catalytic cycle. Mn (III) contributes to the decomposition of hazardous chemicals. Mn (III) forms a complex with malonic acid, which has a maximum absorption at 270 nm. Hence, the difference between the absorption at 270 nm of the test sample and that of the control was used as an indication of enzyme activity.

The results are shown in FIGS. 7–10.

Figure 7:
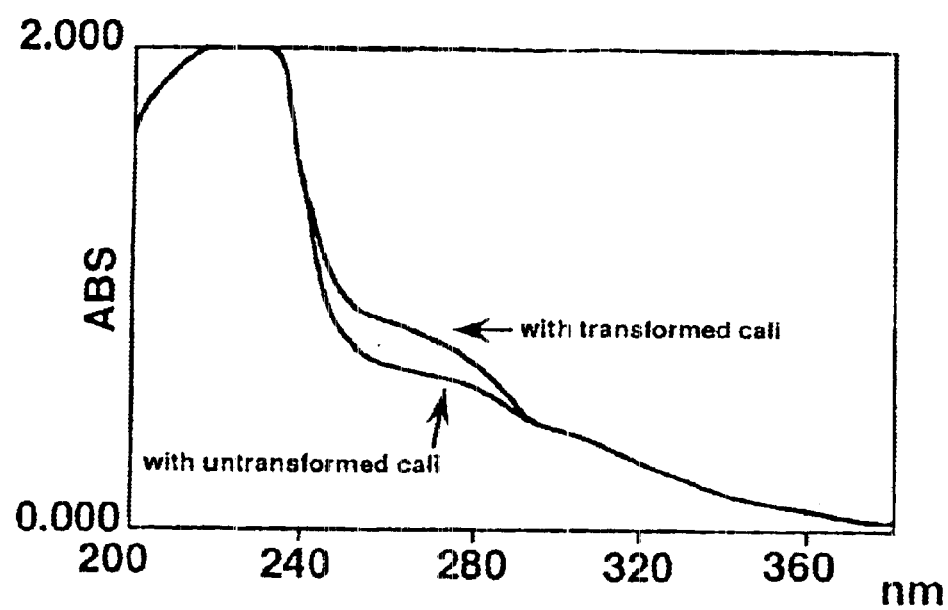
FIG. 7 shows the manganese peroxidase activity in the callus into which the plasmid W35SfMnP/pBI121 is transferred.
Figure 8:
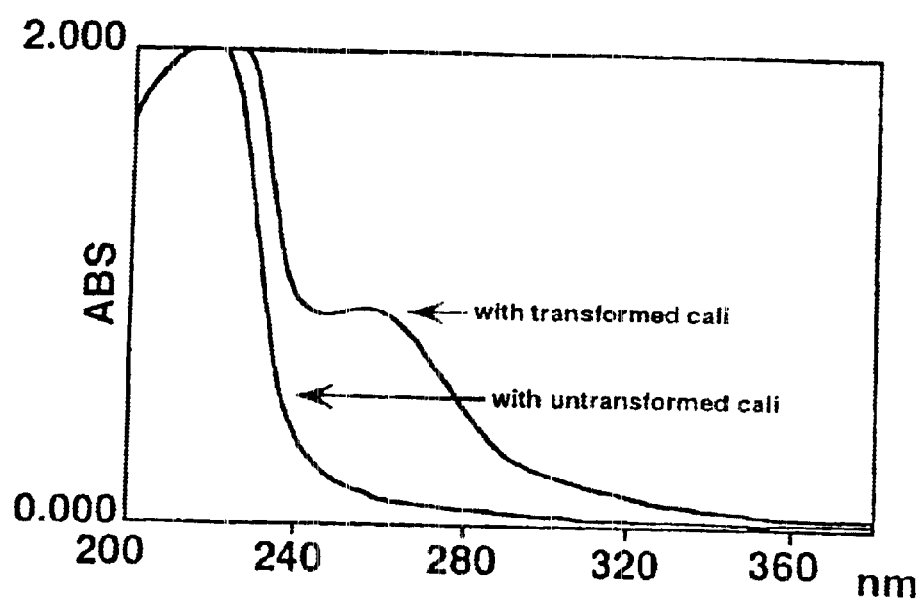
FIG. 8 shows the manganese peroxidase activity in the callus into which the plasmid W35SfMnP6×His/pBI121 is transferred.

The results for the case where the full-length manganese peroxidase gene was transferred, are shown in FIG. 7 and FIG. 8. In spite of individual differences, the maximum absorption at 270 nm was obviously increased compared with the control, thereby confirming that the transformant has manganese peroxidase activity. Furthermore, a transformant into which W35SfMnP6×His/pBI121 had been transferred, was destroyed, and the total protein extracted with 50 mM phosphate buffer (pH 7.5) was used as a sample to perform an Western blotting with a 6×His tag antibody, thereby confirming the generation of the enzyme.

The same reaction was performed for the supernatant after incubating the callus in the Murashige & Skoog complete medium in an attempt to detect manganese peroxidase activity, which brought about a slight increase in absorption. However, the enzyme activity was obviously low compared to that of the callus.

Figure 9:
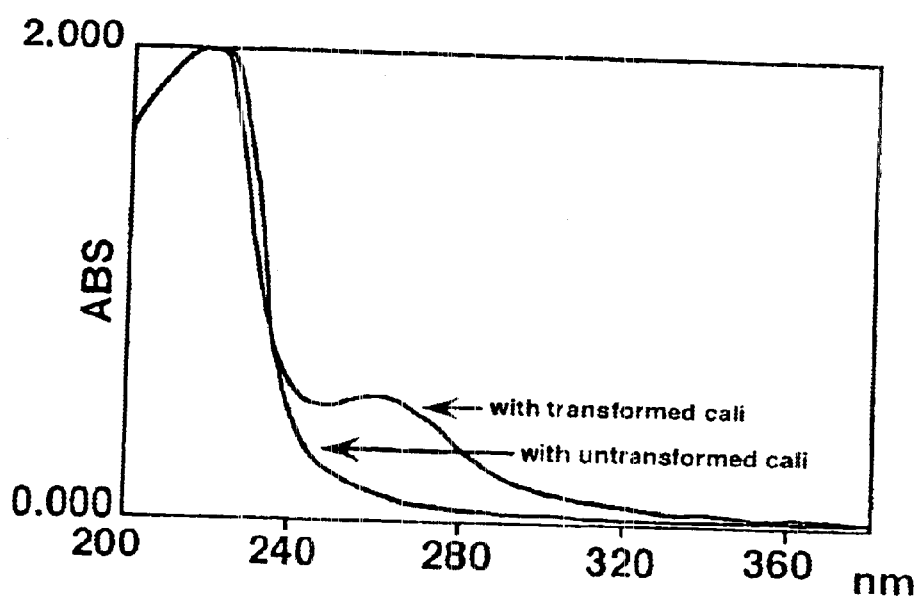
FIG. 9 shows the manganese peroxidase activity in the callus into which the plasmid W35SmMnP/pBI121 is transferred.
Figure 10:
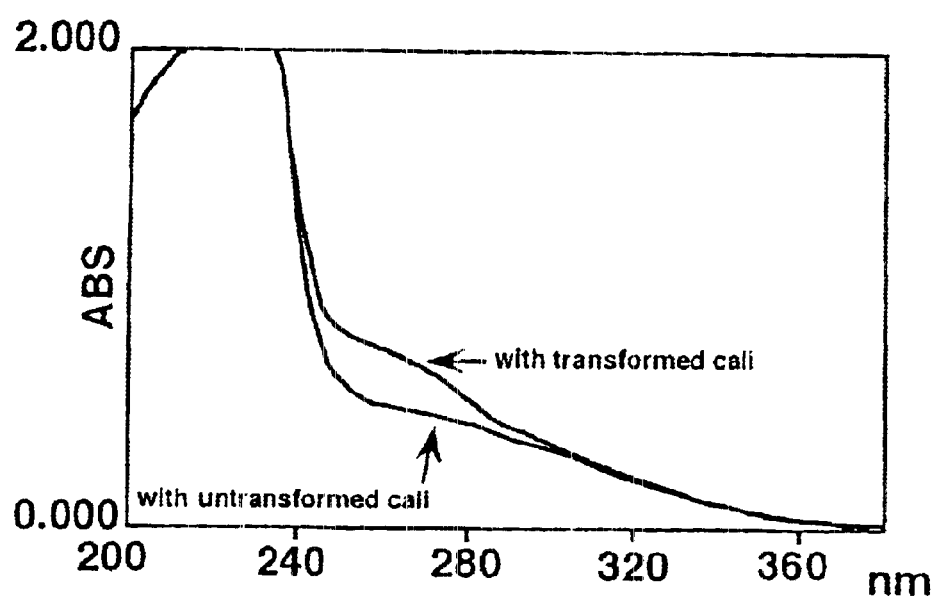
FIG. 10 shows the manganese peroxidase activity in the callus into which the plasmid W35SmMnP6×His/pBI221 is transferred.

The results in case that the manganese peroxidase gene encoding the mature protein was transferred, are shown in FIG. 9 and FIG. 10. The maximum absorption at 270 nm was obviously increased compared to that of the control, thereby confirming that the transformant has the manganese peroxidase activity. Furthermore, a transformant into which W35SmMnP6×His/pBI121 has been transferred, was destroyed, and the total protein extracted with 50 mM phosphate buffer (pH 7.5) was used as a sample to perform the Western blotting with the 6×His tag antibody, thereby confirming the generation of the enzyme.

The same reaction was performed for the supernatant after incubating the callus in the Murashige & Skoog complete medium in an attempt to detect manganese peroxidase activity, which brought about a slight increase in absorption. However, the enzyme activity was obviously low compared to that of the callus.

Example 4

Detection of Manganese Peroxidase Activity in a Transformed Plant

A solution for water culture was prepared, to which a predetermined amount of Hyponex™, and remazol brilliant blue (RBB) as a substrate were added. Then, the transformed plant, which was grown to be about 20 cm long after transferring the manganese peroxidase gene encoding the full-length or mature protein, was planted in this solution. The RBB was decolorized with time, and the color was completely removed after 24 hours.

The transformed plant was incubated with a solution for water culture without adding RBB. Although RBB was added after 24 hours, decolorization was not seen at all. Still further, the addition of horseradish peroxidase to this solution brought about the complete decolorization of RBB.

As stated above, it was demonstrated that the endogenous hydrogen peroxide was released from the roots to the culture solution. Furthermore, it was concluded that the manganese peroxidase produced by the transformed plant into which the manganese peroxidase gene encoding the full-length or mature protein had been transferred, existed on the cell surface of roots.

The same results were obtained from experiments as described above using Ine and poplar into which the gene had not been transferred. The peroxidase that plants originally have, is involved for these cases, and it was demonstrated that the peroxidase existed on the cell surface of roots even in herbage and woody plants, and the endogenous hydrogen peroxide was released from their roots to the culture solution.

Hence, to transfer a basidiomycete-derived peroxidase gene into herbage and woody plants, seems to allow the activation of the basidiomycete-derived peroxidase in the rooting zone of the transformed plants. Furthermore, hazardous chemicals can be decomposed and removed by cultivating these transformed plants in the environmental soils contaminated with, for example, dioxin or PCB.

Example 5

Decomposition of Hazardous Chemicals by the Callus Induced from the Transformed Plant.

A callus was induced from each transformed plant, and the callus of the same wet mass was incubated in Murashige & Skoog complete medium (Physiol Plant, 1962, 15, 473) at 28° C. for 3 days. The callus of the same wet mass was washed 3 times with 50 mM malonate buffer (pH 4.5), and suspended in a fresh malonate buffer. Manganese sulfate and pentachlorophenol (PCP) were added to this suspension to a final concentration of 1 mM, which was then incubated at 37° C. for 16 hours. The PCP, which existed in a certain quantity of the culture supernatant, was determined using high performance liquid chromatography (HPLC). Furthermore, free chloride ions in the culture supernatant were determined by ion chromatography (IC). Still further, a certain quantity of the culture supernatant was acidified with hydrochloric acid (pH 2) to extract a reactive product with acetic acid ethyl ester. The organic layer was dehydrated on anhydrous sodium acetate, which was subjected to condensation, acetylation, and GC-MS analysis.

As a result of HPLC analysis, the PCP was apparently reduced, compared with that of the control, when the callus induced from the transformed plant was added. Results of IC analysis also showed an increase in the amount of the free chloride ions, accompanied by a decrease in PCP. Furthermore, no product except for the PCP could be observed for the control; however, a reaction product considered to be dechlorinated oxidatively, could be seen when the transformed callus was added.

ADVANTAGE OF THE INVENTION

The present invention provides a novel plant into which a basidiomycete-derived peroxidase gene is transferred. The environment contaminated with hazardous chemicals can be decontaminated using this plant.

What is claimed is:

1. A plant into which a DNA comprising the coding sequence of a basidiomycete manganese peroxidase has been transferred, wherein the basidiomycete manganese peroxidase comprises amino acids 27–365 of SEQ ID NO:2, and wherein the basidiomycete manganese peroxidase is expressed in the plant.

2. The plant according to claim 1, wherein the coding sequence of a basidiomycete manganese peroxidase comprises nucleotides 79–1095 of SEQ ID NO:1.

3. The plant according to claim 1, wherein the basidiomycete manganese peroxidase comprises amino acids 1–365 of SEQ ID NO:2.

4. The plant according to claim 3, wherein the coding sequence of a basidiomycete manganese peroxidase comprises nucleotides 1–1095 of SEQ ID NO:1.

5. The plant according to any of claim 1–4, wherein the DNA further comprises the cauliflower mosaic virus 35S promoter (CMV35SP) operably linked to the coding sequence of the basidiomycete manganese peroxidase.

6. The plant according to any of claims 1–4, wherein the plant is a seed plant.

7. The plant according to any of claims 1–4, wherein the basidiomycete manganese peroxidase exists in an active and stable form on the cell surface of the roots of the plant.

8. A method for removing an environmental contaminant from an environment comprising the contaminant, wherein the environmental contaminant can be decomposed by a basidiomycete manganese peroxidase, the method comprising:

(a) transferring a DNA comprising the coding sequence of a basidiomycete manganese peroxidase into a plant, wherein the coding sequence of a basidiomycete manganese peroxidase is selected from:
   (i) a nucleotide sequence that encodes amino acids 27–365 of SEQ ID NO:2;
   (ii) a nucleotide sequence that comprises nucleotides 79–1095 of SEQ ID NO:1;
   (iii) a nucleotide sequence that encodes amino acids 1–365 of SEQ ID NO:2; and
   (iv) a nucleotide sequence that comprises nucleotides 1–1095 of SEQ ID NO:1; and (b) cultivating the plant into which the DNA comprising the coding sequence of a basidiomycete manganese peroxidase has been transferred in the environment comprising the environmental contaminant to decompose the environmental contaminant and thereby remove the environmental contaminant from the contaminated environment.

9. A method for removing an environmental contaminant from an environment comprising the contaminant, wherein the environmental contaminant can be decomposed by a basidiomycete manganese peroxidase, the method comprising:

(a) transferring a DNA comprising the coding sequence of a basidiomycete manganese peroxidase into a plant, wherein the coding sequence of a basidiomycete manganese peroxidase is selected from:
   (i) a nucleotide sequence that encodes amino acids 27–365 of SEQ ID NO:2;
   (ii) a nucleotide sequence that comprises nucleotides 79–1095 of SEQ ID NO:1;
   (iii) a nucleotide sequence that encodes amino acids 1–365 of SEQ ID NO:2; and
   (iv) a nucleotide sequence that comprises nucleotides 1–1095 of SEQ ID NO:1, and wherein the basidiomycete manganese peroxidase exists in an active and stable form on the cell surface of the roots of the plant; and (b) cultivating the plant into which the DNA comprising the coding sequence of a basidiomycete manganese peroxidase has been transferred in the environment comprising the environmental contaminant to decompose the environmental contaminant and thereby remove the environmental contaminant from the contaminated environment.

10. The method according to claim 8, wherein the environmental contaminant is one or more of a chlorophenol, dioxin, an agricultural chemical, a polycyclic aromatic hydrocarbon, an alkylphenol, an aromatic hydrocarbon, or a nitro compound.

11. The method according to claim 8, wherein the environmental contaminant is a chlorophenol.

12. The method according of claim 11, wherein the chlorophenol is pentachlorophenol.

13. The method according to claim 8, wherein the cultivation is accompanied by the addition of Mn (II).

14. The method according to claim 9, wherein the environmental contaminant is one or more of a chlorophenol, dioxin, an agricultural chemical, a polycyclic aromatic hydrocarbon, an alkylphenol, an aromatic hydrocarbon, or a nitro compound.

15. The method according to claim 9, wherein the environmental contaminant is a chlorophenol.

16. The method according of claim 15, wherein the chlorophenol is pentachlorophenol.

17. The method according to claim 9, wherein the cultivation is accompanied by the addition of Mn (II).

18. An isolated plasmid that comprises a coding sequence of a basidiomycete manganese peroxidase, wherein the coding sequence is selected from:

(a) a nucleotide sequence that encodes amino acids 27–365 of SEQ ID NO:2;

(b) a nucleotide sequence that comprises nucleotides 79–1095 of SEQ ID NO:1;

(c) a nucleotide sequence that encodes amino acids 1–365 of SEQ ID NO:2; and a nucleotide sequence that comprises nucleotides 1–1095 of SEQ ID NO:1.

* * * * *

UNITED STATES PATENT AND TRADEMARK OFFICE
CERTIFICATE OF CORRECTION

PATENT NO.    : 6,642,439 B2
DATED         : November 4, 2003
INVENTOR(S)   : Yosuke Iimura et al.

It is certified that error appears in the above-identified patent and that said Letters Patent is hereby corrected as shown below:

Column 15,
Line 17, "claim" should read -- claims --.

Column 16,
Line 29, "according of claim" should read -- according to claim --.

Signed and Sealed this

Thirtieth Day of December, 2003

JAMES E. ROGAN
*Director of the United States Patent and Trademark Office*

SEQUENCE LISTING

<160> NUMBER OF SEQ ID NOS: 6

<210> SEQ ID NO 1
<211> LENGTH: 1098
<212> TYPE: DNA
<213> ORGANISM: Coriolus versicolor
<220> FEATURE:
<221> NAME/KEY: CDS
<222> LOCATION: (1)..(1095)

<400> SEQUENCE: 1

| | | | | | | | | | | | | | | | | |
|---|---|---|---|---|---|---|---|---|---|---|---|---|---|---|---|---|
| atg | gct | ttc | aaa | act | ctc | gcc | tct | ctc | ctc | tcg | gtt | ctg | gtc | acc | atc | 48 |
| Met | Ala | Phe | Lys | Thr | Leu | Ala | Ser | Leu | Leu | Ser | Val | Leu | Val | Thr | Ile | |
| 1 | | | | 5 | | | | | 10 | | | | | 15 | | |

| cag | gtc | gca | agc | ggc | gcg | ctc | acc | cgc | cgt | gtc | gcc | tgc | ccc | gac | ggc | 96 |
|---|---|---|---|---|---|---|---|---|---|---|---|---|---|---|---|---|
| Gln | Val | Ala | Ser | Gly | Ala | Leu | Thr | Arg | Arg | Val | Ala | Cys | Pro | Asp | Gly | |
| | | | 20 | | | | | 25 | | | | | 30 | | | |

| gtg | aac | acc | gct | acc | aac | gcg | gcg | tgc | tgc | cag | ctc | ttc | gct | gtc | cgc | 144 |
|---|---|---|---|---|---|---|---|---|---|---|---|---|---|---|---|---|
| Val | Asn | Thr | Ala | Thr | Asn | Ala | Ala | Cys | Cys | Gln | Leu | Phe | Ala | Val | Arg | |
| | | 35 | | | | | 40 | | | | | 45 | | | | |

| gac | gac | atc | cag | cag | aac | ctg | ttc | gat | ggc | ggc | gag | tgt | ggc | gag | gag | 192 |
|---|---|---|---|---|---|---|---|---|---|---|---|---|---|---|---|---|
| Asp | Asp | Ile | Gln | Gln | Asn | Leu | Phe | Asp | Gly | Gly | Glu | Cys | Gly | Glu | Glu | |
| | 50 | | | | | 55 | | | | | 60 | | | | | |

| gtc | cac | gag | tcc | ctc | cgt | ctg | acc | ttc | cac | gac | gcc | atc | ggc | atc | tct | 240 |
|---|---|---|---|---|---|---|---|---|---|---|---|---|---|---|---|---|
| Val | His | Glu | Ser | Leu | Arg | Leu | Thr | Phe | His | Asp | Ala | Ile | Gly | Ile | Ser | |
| 65 | | | | | 70 | | | | | 75 | | | | | 80 | |

| cct | tcc | atc | gcc | tcc | cgc | ggc | caa | ttc | ggg | ggc | gga | ggt | gcc | gac | ggc | 288 |
|---|---|---|---|---|---|---|---|---|---|---|---|---|---|---|---|---|
| Pro | Ser | Ile | Ala | Ser | Arg | Gly | Gln | Phe | Gly | Gly | Gly | Gly | Ala | Asp | Gly | |
| | | | | 85 | | | | | 90 | | | | | 95 | | |

| tcc | atc | gcc | ctc | ttt | gag | gac | atc | gag | acc | aac | ttc | cac | gcc | aac | ctc | 336 |
|---|---|---|---|---|---|---|---|---|---|---|---|---|---|---|---|---|
| Ser | Ile | Ala | Leu | Phe | Glu | Asp | Ile | Glu | Thr | Asn | Phe | His | Ala | Asn | Leu | |
| | | | 100 | | | | | 105 | | | | | 110 | | | |

| ggt | gtc | gac | gag | atc | atc | gac | gag | cag | cgg | ccg | ttc | atc | gcc | cgc | cac | 384 |
|---|---|---|---|---|---|---|---|---|---|---|---|---|---|---|---|---|
| Gly | Val | Asp | Glu | Ile | Ile | Asp | Glu | Gln | Arg | Pro | Phe | Ile | Ala | Arg | His | |
| | | 115 | | | | | 120 | | | | | 125 | | | | |

| aac | ctc | acc | acc | gcc | gac | ttc | atc | cag | ttc | gcc | ggc | gcc | atc | ggt | gtc | 432 |
|---|---|---|---|---|---|---|---|---|---|---|---|---|---|---|---|---|
| Asn | Leu | Thr | Thr | Ala | Asp | Phe | Ile | Gln | Phe | Ala | Gly | Ala | Ile | Gly | Val | |
| | 130 | | | | | 135 | | | | | 140 | | | | | |

| agc | aac | tgc | ccc | ggc | gcg | ccc | cag | ctg | gac | gtg | ttc | atc | ggc | cgc | ccc | 480 |
|---|---|---|---|---|---|---|---|---|---|---|---|---|---|---|---|---|
| Ser | Asn | Cys | Pro | Gly | Ala | Pro | Gln | Leu | Asp | Val | Phe | Ile | Gly | Arg | Pro | |
| 145 | | | | | 150 | | | | | 155 | | | | | 160 | |

| gac | gcg | acg | cag | ccc | gcg | ccc | gac | ctg | acc | gtg | ccc | gag | ccg | ttc | gac | 528 |
|---|---|---|---|---|---|---|---|---|---|---|---|---|---|---|---|---|
| Asp | Ala | Thr | Gln | Pro | Ala | Pro | Asp | Leu | Thr | Val | Pro | Glu | Pro | Phe | Asp | |
| | | | | 165 | | | | | 170 | | | | | 175 | | |

| acc | gtc | gac | agc | atc | atc | gag | cgg | ttc | tcc | gac | gcg | ggc | ggc | ttc | acg | 576 |
|---|---|---|---|---|---|---|---|---|---|---|---|---|---|---|---|---|
| Thr | Val | Asp | Ser | Ile | Ile | Glu | Arg | Phe | Ser | Asp | Ala | Gly | Gly | Phe | Thr | |
| | | | 180 | | | | | 185 | | | | | 190 | | | |

| ccc | gcg | gag | atc | gtc | gcg | ctt | ctc | gtg | tcg | cac | acg | atc | gcc | gcg | gcc | 624 |
|---|---|---|---|---|---|---|---|---|---|---|---|---|---|---|---|---|
| Pro | Ala | Glu | Ile | Val | Ala | Leu | Leu | Val | Ser | His | Thr | Ile | Ala | Ala | Ala | |
| | | 195 | | | | | 200 | | | | | 205 | | | | |

| gac | cac | gtc | gac | ccg | agc | atc | ccc | gga | acg | ccc | ttc | gac | tcg | acc | ccg | 672 |
|---|---|---|---|---|---|---|---|---|---|---|---|---|---|---|---|---|
| Asp | His | Val | Asp | Pro | Ser | Ile | Pro | Gly | Thr | Pro | Phe | Asp | Ser | Thr | Pro | |
| | 210 | | | | | 215 | | | | | 220 | | | | | |

| gag | gag | ttc | gac | acg | cag | ttc | ttc | atc | gag | acg | cag | ctc | cgc | ggc | acg | 720 |
|---|---|---|---|---|---|---|---|---|---|---|---|---|---|---|---|---|
| Glu | Glu | Phe | Asp | Thr | Gln | Phe | Phe | Ile | Glu | Thr | Gln | Leu | Arg | Gly | Thr | |
| 225 | | | | | 230 | | | | | 235 | | | | | 240 | |

| ctc | ttc | ccc | ggc | acc | ggc | ggc | aac | cag | ggc | gag | gtc | gag | tcc | ccc | ctc | 768 |
|---|---|---|---|---|---|---|---|---|---|---|---|---|---|---|---|---|
| Leu | Phe | Pro | Gly | Thr | Gly | Gly | Asn | Gln | Gly | Glu | Val | Glu | Ser | Pro | Leu | |
| | | | | 245 | | | | | 250 | | | | | 255 | | |

```
cgc ggc gag ctg cgc ctc cag tcc gac tct gag ctc gcg cgc gac tct    816
Arg Gly Glu Leu Arg Leu Gln Ser Asp Ser Glu Leu Ala Arg Asp Ser
            260                 265                 270 cgc act gct tgc gag tgg cag tcc ttc gtc aac aac cag gcc aag ctc    864
Arg Thr Ala Cys Glu Trp Gln Ser Phe Val Asn Asn Gln Ala Lys Leu
            275                 280                 285 cag tcc gcg ttc aag gct gcc ttc cgc aag atg acc gtg ctc ggc cac    912
Gln Ser Ala Phe Lys Ala Ala Phe Arg Lys Met Thr Val Leu Gly His
        290                 295                 300 gac gag agc ctg ctg atc gag tgc tcc gag ctc gtg ccc acg cct ccg    960
Asp Glu Ser Leu Leu Ile Glu Cys Ser Glu Leu Val Pro Thr Pro Pro
305                 310                 315                 320 ccg gcg acg agc gtc gcg cac ttc ccc gct ggg ctc agc aac gcc gac   1008
Pro Ala Thr Ser Val Ala His Phe Pro Ala Gly Leu Ser Asn Ala Asp
                325                 330                 335 gtc gag cag gcg tgc gcc gac acc ccc ttc ccg acg ctc ccc acc gac   1056
Val Glu Gln Ala Cys Ala Asp Thr Pro Phe Pro Thr Leu Pro Thr Asp
                340                 345                 350 cct gga ccc gtc acc acc gtc gcc ccc gtc ccc ccg tcg taa            1098
Pro Gly Pro Val Thr Thr Val Ala Pro Val Pro Pro Ser
                355                 360                 365

<210> SEQ ID NO 2
<211> LENGTH: 365
<212> TYPE: PRT
<213> ORGANISM: Coriolus versicolor

<400> SEQUENCE: 2

Met Ala Phe Lys Thr Leu Ala Ser Leu Leu Ser Val Leu Val Thr Ile
 1               5                  10                  15

Gln Val Ala Ser Gly Ala Leu Thr Arg Arg Val Ala Cys Pro Asp Gly
            20                  25                  30

Val Asn Thr Ala Thr Asn Ala Ala Cys Cys Gln Leu Phe Ala Val Arg
        35                  40                  45

Asp Asp Ile Gln Gln Asn Leu Phe Asp Gly Gly Glu Cys Gly Glu Glu
    50                  55                  60

Val His Glu Ser Leu Arg Leu Thr Phe His Asp Ala Ile Gly Ile Ser
65                  70                  75                  80

Pro Ser Ile Ala Ser Arg Gly Gln Phe Gly Gly Gly Ala Asp Gly
                85                  90                  95

Ser Ile Ala Leu Phe Glu Asp Ile Glu Thr Asn Phe His Ala Asn Leu
                100                 105                 110

Gly Val Asp Glu Ile Ile Asp Glu Gln Arg Pro Phe Ile Ala Arg His
            115                 120                 125

Asn Leu Thr Thr Ala Asp Phe Ile Gln Phe Ala Gly Ala Ile Gly Val
        130                 135                 140

Ser Asn Cys Pro Gly Ala Pro Gln Leu Asp Val Phe Ile Gly Arg Pro
145                 150                 155                 160

Asp Ala Thr Gln Pro Ala Pro Asp Leu Thr Val Pro Glu Pro Phe Asp
                165                 170                 175

Thr Val Asp Ser Ile Ile Glu Arg Phe Ser Asp Ala Gly Gly Phe Thr
            180                 185                 190

Pro Ala Glu Ile Val Ala Leu Leu Val Ser His Thr Ile Ala Ala Ala
        195                 200                 205

Asp His Val Asp Pro Ser Ile Pro Gly Thr Pro Phe Asp Ser Thr Pro
    210                 215                 220
```

Glu Glu Phe Asp Thr Gln Phe Phe Ile Glu Thr Gln Leu Arg Gly Thr
225                 230                 235                 240

Leu Phe Pro Gly Thr Gly Gly Asn Gln Gly Glu Val Glu Ser Pro Leu
            245                 250                 255

Arg Gly Glu Leu Arg Leu Gln Ser Asp Ser Glu Leu Ala Arg Asp Ser
            260                 265                 270

Arg Thr Ala Cys Glu Trp Gln Ser Phe Val Asn Asn Gln Ala Lys Leu
            275                 280                 285

Gln Ser Ala Phe Lys Ala Ala Phe Arg Lys Met Thr Val Leu Gly His
            290                 295                 300

Asp Glu Ser Leu Leu Ile Glu Cys Ser Glu Leu Val Pro Thr Pro Pro
305                 310                 315                 320

Pro Ala Thr Ser Val Ala His Phe Pro Ala Gly Leu Ser Asn Ala Asp
            325                 330                 335

Val Glu Gln Ala Cys Ala Asp Thr Pro Phe Pro Thr Leu Pro Thr Asp
            340                 345                 350

Pro Gly Pro Val Thr Thr Val Ala Pro Val Pro Pro Ser
            355                 360                 365

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
ttgtttctag atggctttca aaactctcgc                              30

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
aatctctaga tggtcgcctg cccctacgga gtg                          33

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5
aattggatcc ttacgacggg gggacggggg                              30

<210> SEQ ID NO 6
<211> LENGTH: 65
<212> TYPE: DNA
<213> ORGANISM: Artificial Sequence
<220> FEATURE:
<223> OTHER INFORMATION: Primer

<400> SEQUENCE: 6
aattggatcc tcagtggtgg tggtggtggt ggtgcgacgg ggggacgggg gcgacggtgg    60
tgacg                                                              65